United States Patent [19]

Denance

[11] Patent Number: 4,512,767
[45] Date of Patent: Apr. 23, 1985

[54] APPARATUS FOR PERFORMING INTRADERMAL, SUBCUTANEOUS OF INTRAMUSCULAR INJECTIONS

[76] Inventor: Raymond Denance, Le Marineland, 2170 Rte. de la Corniche, 83700 Boulouris St. Raphael, France

[21] Appl. No.: 480,327

[22] Filed: Mar. 30, 1983

[30] Foreign Application Priority Data

Mar. 30, 1982 [FR] France ............................. 82 05380

[51] Int. Cl.³ .............................................. A61M 5/00
[52] U.S. Cl. ..................................... 604/137; 604/208
[58] Field of Search ............... 604/136, 137, 117, 156, 604/157, 181, 187, 207, 208, 209, 223, 224, 211

[56] References Cited

U.S. PATENT DOCUMENTS

| | | | |
|---|---|---|---|
| 2,591,457 | 4/1952 | Maynes | 604/137 |
| 3,064,650 | 11/1962 | Lewis | 604/136 |
| 3,494,358 | 2/1970 | Fehus et al. | 604/137 |
| 3,790,048 | 2/1974 | Luciano . | |
| 4,198,975 | 4/1980 | Haller . | |
| 4,333,459 | 6/1982 | Becker | 604/136 |
| 4,403,989 | 9/1983 | Christensen et al. | 604/137 |

Primary Examiner—John D. Yasko
Attorney, Agent, or Firm—Young & Thompson

[57] ABSTRACT

An injection device useful either for manual injection or mechanical injection, comprises a cross frame having the shape of a revolver. A removable injection syringe having a syringe piston and at least one needle, is mounted on the cross frame, and a syringe cradle secures the syringe to the cross frame. A device is provided for positioning the penetration and to predetermine the degree of penetration of the needle. There is a trigger on the cross frame, and a pawl is actuated by the trigger. The pawl rotates a barrel step by step upon repeated actuation of the trigger. A screw-threaded axle is rotated by the barrel, and a screw-threaded slider is in screw-threaded engagement with the screw-threaded axle and moves forward upon rotation of the axle. The slider and the syringe piston are interconnected to advance the syringe piston stepwise upon repeated actuation of the trigger.

3 Claims, 1 Drawing Figure

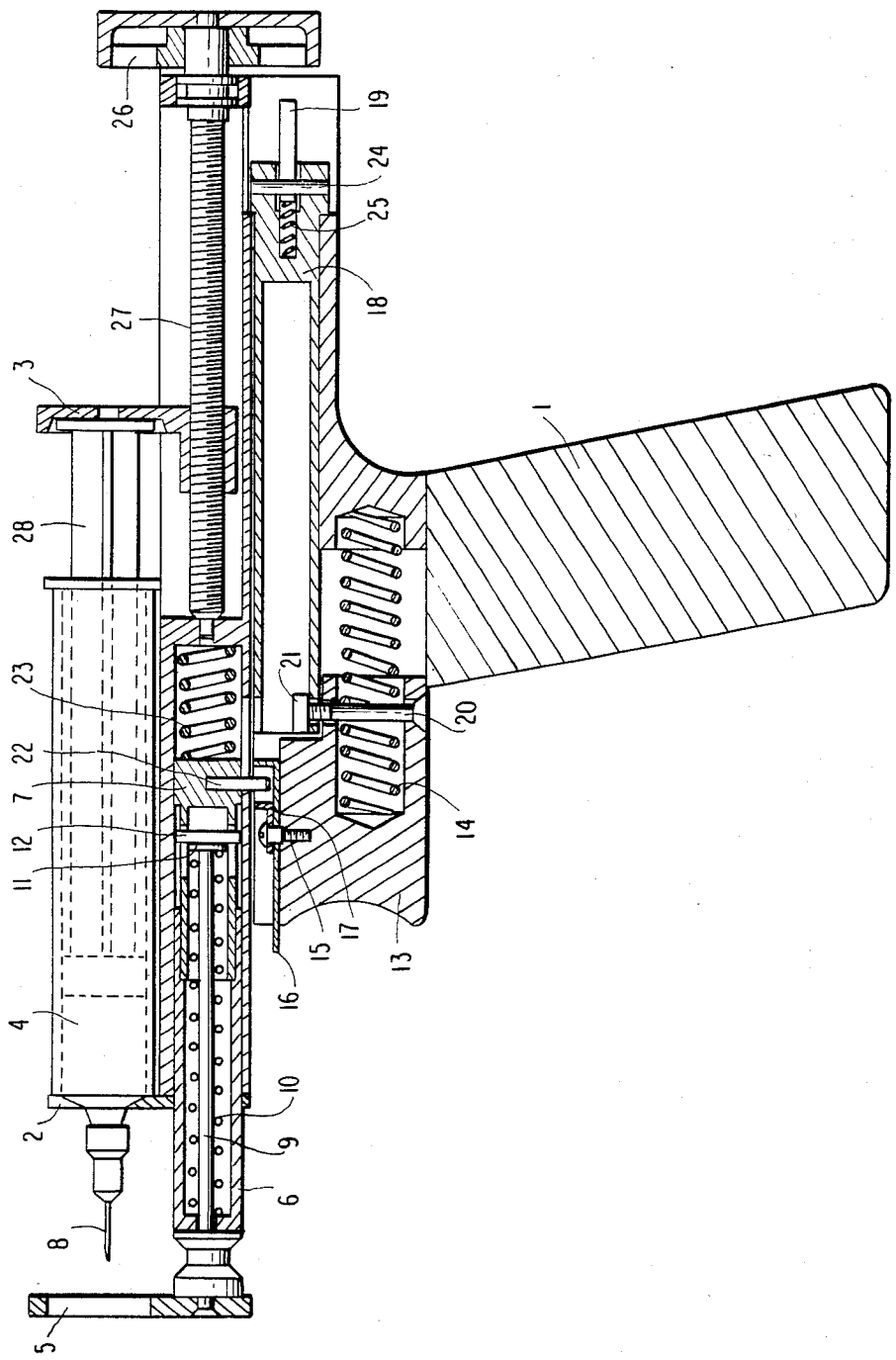

APPARATUS FOR PERFORMING INTRADERMAL, SUBCUTANEOUS OF INTRAMUSCULAR INJECTIONS

The present invention has for its object an apparatus for performing intradermal, subcutaneous or intramuscular injections for medical or veterinary use, and more particularly in meso-therapy, hydropuncture, vaccinations or allergy tests.

The devices known up to now to perform automatic injections require complicated and cumbersome electrically or pneumatically operated devices which reduce their mobility, and are therefore generally used at fixed positions.

Moreover these devices have the following drawbacks:
- the weight of the apparatus severely limits the period of use by the practitioner.
- the absence of precision in the location of the injection and in the degree of penetration.
- the source of operating energy connected to the body of the device prevents complete mobility in use.

This new form of injector has the following technical advantages:
- no need for an external energy source (electrical, electromagnetic, pneumatic, thermal or electronic).
- is easily transportable, being of light weight and small volume. Can be carried in a clothing pocket.
- the technical conception is simple and reliable, it avoids the risk of failure frequently encountered with known techniques.
- permits complete mobility of use in a medical office or any other place.
- possibility of interchangeability of syringes of different types quickly and easily.

In accordance with the desired end, the injections may be single or multiple, precise and predetermined as to volume particularly in the case of mass vaccinations.

Several advantages of the injection aimer on this apparatus may be enumerated:
- precision as to the point of treatment or of the place of injection.
- stabilization of the skin at the desired position in the region to be treated, permitting perpendicular or oblique injections.
- pressure of the injection aimer on the skin facilitates and renders more painless the penetration of the needle by a medullary inhibition of the receipt of the pain signal.

The present device is comprised by a metallic or plastic cross frame 1 (see the drawing) on which is disposed, between the conical stirrup 2 and the slider 3, a syringe 4 which may be of various dimensions.

The injection aimer 5 pre-adjusted by a micrometer screw comprised by a milled cylinder 6 and a plug 7 adapted to be displaceable in a bore provided in the cross frame 1 permits determining exactly the penetration of the needle 8. The injection aimer and its support axle 9 are maintained in position by a spring 10, a guide 11, and a pin 12 which can move in the opening in the plug 7 during adjustment of the micrometer screw.

A trigger 13 having a return spring 14, a screw 15 serving as an axle of rotation, a catch 16 and securing an abutment 17 is integral with a control member 18 of the pawl 19 serving to actuate a drum 26 which drives the rotation of a threaded axle 27 and the displacement of slider 3, having the same screw thread, by means of the screw 20 and its nut 21.

The device may be used for injections of the type "manual or mechanical". By manual injection is meant the injection which is actuated by pressure exerted on the trigger, and by mechanical injection, the injection automatically triggered by simple pressure of the aimer on the region to be treated.

The choice of type of injection "manual or mechanical" of the apparatus is determined by the position of the catch 16, which by rotation about the axle 15 drives or frees the control pin 22 of plug 27 according to the desired adjusted position.

When using the device for manual injection, the position of the catch 16 frees control pin 22 from plug 7, from the milled cylinder 6 and from the injection aimer 5.

Use of the apparatus takes place by pushing the cross frame 1 toward the injection aimer 5 applied to the region to be treated, effecting its retraction into the bore of the cross frame 1 as well as the penetration of the needle 8 determined by adjustment of the aimer.

The invention is practiced by a single pull or repeated pulls on the trigger 13 according to the volume to be injected. A return spring 23 restores the assembly of plug 7, cylinder 6, injection aimer 5 to its rest position.

When using the apparatus for mechanical injection, the position of the catch 6 renders unitary the assembly of the injection aimer 5, the milled cylinder 6, plug 7 with its pin 22 and trigger 13. The operation of the device is effected by pressures and repeated displacements of the cross frame 1 toward the injection aimer 5 applied to the region to be treated provoking the recoil of the latter into the bore of the cross frame 1, and simultaneously the penetration of needle 8 and injection of the chosen liquid. A return spring 23 restores the assembly of plug 7, cylinder 6, injection aimer 5 to its rest position.

No matter what the mode of use chosen for the apparatus, manual or mechanical injection, the injection will take place by means of the assembly of control means 18, pawl 19 having an axle 24 and a return spring 25 serving as a brake which, moving rearwardly of the apparatus, engaged pawl 19 in a drum 26 and effects relative rotative movement of the latter and its screw threaded axle 27 and advances the slider 3 forwardly of the apparatus producing a pressure on piston 28 in the body of the syringe 4.

Each movement of rotation of the barrel produces a fixed advance of the slider 3 which results in an injection of constant volume. The injected volume with each pressure is a function of the section of the syringe, of the thread pitch of slider 3 and of the screw 27, of the profile of drum 26.

The use of the device requires, during filling of the syringe, successive actuations of trigger 13 permitting the coming into contact of slider 3 and the rear of piston 28 of the syringe, and the elimination of air pockets that might be found in the body of syringe 4.

I claim:

1. An injection device useful either for manual injection or mechanical injection, comprising a cross frame (1) having the shape of a revolver, a removable injection syringe (4) having a syringe piston and at least one needle (8), a syringe cradle securing said syringe to the cross frame (1), means to position the penetration and to predetermine the degree of penetration of said at least one needle, a trigger (13) on the cross frame, a pawl (19)

actuated by the trigger, a barrel (26) that is rotated step by step by the pawl upon repeated actuation of the trigger, a screw-threaded axle (27) rotated by the barrel, a screw-threaded slider (3) that is in screw-threaded engagement with said screw-threaded axle (27) and that moves forward upon rotation of said axle, and means (28) interconnecting said slider (3) and said syringe piston to advance said syringe piston stepwise upon repeated actuation of said trigger (13).

2. An injection device as claimed in claim 1, in which said means to position the penetration and to determine the degree of penetration of said at least one needle comprises an injection aimer (5) secured to a support (9), a guide (11), a pin (12), and adjustment means permitting positioning the penetration of said at least one needle and predetermining the degree of penetration of said at least one needle.

3. An injection device as claimed in claim 1, and a screw (15) carried by said trigger serving as the axle for a latch (16) and securing an abutment (17) to a control member (18) for actuating said pawl, said latch being positionable selectively to connect or disconnect said trigger to said pawl.

* * * * *